United States Patent [19]
Brett

[11] Patent Number: 5,948,400
[45] Date of Patent: Sep. 7, 1999

[54] METHOD OF APPLYING A PRESSURE-SENSITIVE ADHESIVE WOUND DRESSING AND WATER-BASED SKIN TREATMENT COMPOSITION

[75] Inventor: David W. Brett, St. Petersburg, Fla.

[73] Assignee: Smith & Nephew Inc., Memphis, Tenn.

[21] Appl. No.: 08/974,891

[22] Filed: Nov. 20, 1997

[51] Int. Cl.$^6$ .................................................. A61K 31/795
[52] U.S. Cl. ..................... 424/78.03; 424/78.05; 424/78.06; 424/78.07; 514/506; 514/532; 514/546; 514/944
[58] Field of Search ................... 424/443, 78.37, 424/78.03, 78.02, 78.05, 78.06, 78.07; 514/506, 532, 546, 944

[56] References Cited

U.S. PATENT DOCUMENTS

| | | | |
|---|---|---|---|
| Re. 34,682 | 8/1994 | Vishnupad et al. | 524/601 |
| Re. 34,716 | 9/1994 | Vishnupad et al. | 524/601 |
| 3,546,008 | 12/1970 | Shields et al. | 117/138.8 |
| 3,734,874 | 5/1973 | Kibler et al. | 260/29.2 E |
| 3,779,993 | 12/1973 | Kibler et al. | 260/75 S |
| 3,928,556 | 12/1975 | Sweger | 424/45 |
| 3,932,602 | 1/1976 | Sweger | 424/45 |
| 4,233,196 | 11/1980 | Sublett | 260/29.2 |
| 4,942,029 | 7/1990 | Scheps | 424/78 |
| 4,950,475 | 8/1990 | Vishnupad et al. | 424/83 |
| 4,987,893 | 1/1991 | Salamone et al. | 128/156 |
| 5,103,812 | 4/1992 | Salamone et al. | 602/52 |
| 5,266,322 | 11/1993 | Myers et al. | 424/401 |
| 5,534,247 | 7/1996 | Franjac et al. | 424/707 |
| 5,599,524 | 2/1997 | Morawsky et al. | 424/47 |

OTHER PUBLICATIONS

Product Brochure: "3M No Sting Barrier Film", 3M Healthcare, St. Paul, Minnesota (2 pages) 1995.

Product Packaging: "Bard Product and Barrier Film", Single Use Wipes, Catalog No. 740013 (1 page), Bard Patient Care Division, CR Bard Inc., Murray Hill, New Jersey, Apr. 1992.

Product Packaging: "ALLKARE Protective Barrier Wipe", 100 wipes, Order No. 37444 (1 page), ConvaTec, a Bristol–Myer–Squibb Company, Princeton, New Jersey, 1993.

Product Brochure: "Cosmetic Ingredients", Eastman AQ55S and Eastman AQ58S (8 pages), Eastman Chemical Company, 1944.

*Primary Examiner*—Jose' G. Dees
*Assistant Examiner*—Michael A. Williamson
*Attorney, Agent, or Firm*—Larson & Taylor

[57] ABSTRACT

A coating of a liquid, non-stinging, water-based skin treatment composition is applied to skin adjacent a wound and allowed to form a dry film prior to applying a pressure sensitive dressing over the wound. The aqueous composition includes a water dispersible film forming polyester resin and may be formulated with no volatile organic solvents for the resin. The dried film bonds strongly to the pressure sensitive adhesive of the dressing but is relatively easily removed from the skin and thus serves to reduce the force needed to remove the dressing from the skin.

16 Claims, No Drawings

METHOD OF APPLYING A PRESSURE-SENSITIVE ADHESIVE WOUND DRESSING AND WATER-BASED SKIN TREATMENT COMPOSITION

FIELD OF THE INVENTION

The present invention relates to the application of a wound dressing which bears a pressure-sensitive adhesive layer intended to adhere the dressing to the skin, and to a liquid, non-stinging water-based skin treatment composition which is used to prepare the skin for the application of the dressing.

BACKGROUND OF THE INVENTION

Wound dressings that are adhered to human skin by pressure-sensitive adhesive have been known for many years. Such dressings are generally in the form of a web of an appropriate size for the wound and bear a pressure-sensitive adhesive layer intended to adhere the dressing to skin adjacent to the wound to secure the dressing in place over the wound. The webs are made of various materials such as film, foam, fabric, and combinations of these materials. The pressure-sensitive adhesive layer may be continuous or discontinuous and may be configured to adhere to the skin surrounding the wound or to portions of skin surrounding the wound. In many dressings, the adhesive layer is substantially coextensive with the dressing and thus extends over the wound itself. In such dressings, the adhesives are intended to adhere to healthy skin outside the wound and to not adhere to the wound itself due to its inherent moisture. It is also known to provide a coating adjacent to the wound prior to application of a pressure-sensitive adhesive dressing. Such commercially available compositions of this type include a film-forming polymer such as a methacrylate and a major amount of an organic solvent such as isopropyl alcohol or hexamethyl disiloxane. When dried, the film provides a coating to which the pressure-sensitive adhesive dressing is applied. Some of these commercially available compositions provide coatings to which the dressing are tenaciously adhered while others provide coatings from which dressings are easily removed. However, both of these commercially available compositions contain major quantities of volatile organic components such as isopropyl alcohol and hexamethyl disiloxane.

It is also known to provide coatings to human skin for various purposes such as wound protection, wound healing, medicament delivery, skin treatment, sun protection and the like. U.S. Pat. No. 4,942,029 relates to a medicated composition applied to the skin to form an antimicrobial barrier, the composition including a film-forming acrylic copolymer and isopropyl alcohol solvent. U.S. Pat. Nos. 4,987,893 and 5,103,812 relate to non-stinging, non-irritating liquid coating compositions for forming films which act as conformable bandages adhering to and protecting nails, skin and mucous membrane wounds. The compositions are made up of a siloxane containing polymer and a solvent system containing volatile organic siloxanes. U.S. Pat. Nos. 3,928,556 and 3,932,602 relate to a non-stinging wound dressing compositions made up of a film forming acrylate polymer dissolved in a solvent system of stinging and non-stinging volatile organic solvents.

It is an object of the present invention to provide a method of applying a pressure-sensitive adhesive dressing to a wound by first preparing the skin adjacent to the wound by applying a liquid, water-based, non-stinging skin treatment composition which dries to form an adherent polymeric film on the skin, and thereafter applying a pressure-sensitive dressing to the wound to cause the dressing to adhere to the polymeric film.

It is still a further object to provide such a method in which the liquid non-stinging water-based skin treatment composition dries rapidly, preferably in less than 90 seconds, more preferably in less than a minute, and still more preferably in less than 45 seconds, to form a comfortable and adherent protective coating which does not cause binding of the skin and which is easily removed by washing with water.

It is a further object of the present invention to provide a liquid, non-stinging water-based skin treatment composition which is useful for the method of the invention and for other purposes.

It is a further object of the invention to provide an applicator for applying such liquid, non-stinging, water-based skin treatment composition to the skin.

BRIEF SUMMARY OF THE INVENTION

The foregoing and other objects which will be apparent to those of ordinary skill in the art are achieved in accordance with the invention by providing:

(1) a method of applying a pressure-sensitive adhesive dressing to a wound which comprises:
 a) applying to skin adjacent to a wound a liquid, non-stinging, water-based skin treatment composition comprising a water-dispersible film-forming polyester resin, at least one polyol plasticizer, and water, said composition being freely pourable at room temperature to form a coating of said aqueous liquid composition on said skin;
 b) allowing the aqueous liquid composition to dry to from a dried adherent polymeric film on said skin, said film comprising the polyester resin and the plasticizer; and
 c) applying a pressure-sensitive adhesive dressing to the wound by pressing the dressing against the dried film to cause the dressing to adhere to the film;

(2) a liquid, non-stinging, water-based skin treatment composition, said composition being freely pourable at room temperature and consisting essentially of:
water;
a water-dispersible linear polyester having recurring sodiosulfo units of the general formula:

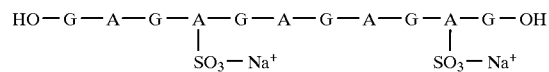

wherein A is an aromatic dicarboxylic acid moiety and G is an aliphatic or cycloaliphatic glycol residue and having a glass transition temperature of from 30 to 60° C.; and
at least one polyol plasticizer in an amount of from 0.5 to 20% by weight based on the weight of the polyester, said polyester being present in an amount of from 20 to 35% by weight based on the total weight of the polyester, the plasticizer, and water; and (3) an applicator for applying the skin treatment composition to skin.

DESCRIPTION OF PREFERRED EMBODIMENTS

The skin treatment composition can be applied to the skin adjacent to the wound in any of several known ways of applying liquid skin-treatment compositions, such as by wipe, swab or brush.

The composition is very liquid and freely pourable at room temperature. The viscosity of the composition at 72° F. is preferably not greater than 1000 cps, is more preferably not greater than 500 cps, and still more preferably not greater than 100 cps. The pH of the composition is either neutral or acidic, and preferably in the range of pH 5–7. The compositions are homogenous and remain homogenous when stored at temperature not exceeding about 80° F. for at least a year. The composition can be applied by being brushed on the skin by a brush or sponge applicator or the like or by a wipe or swab or other applicator which is impregnated with the liquid composition. For example, a skin wipe may be prepared by impregnating a fabric or paper web material with the composition and packaging in an air-tight container to inhibit drying out and to prevent contamination. Suitable packaging material is a three-ply foil laminate having an outer paper layer, an intermediate polypropylene layer, and an inner layer of SURLYN® thermoplastic polymer.

After application of the composition, it is dried, preferably under ambient conditions. Drying may be accelerated, such as by applying heat or by reducing relative humidity. Drying time of the composition, under quiescent ambient conditions at room temperature (72° F.) at a relative humidity of 60%, is preferably less than 90 seconds, more preferably less than 60 seconds, and more preferably less than 45 seconds.

The composition is preferably applied to skin adjacent to a wound and not to the wound itself. However, it is a distinct advantage of the invention that the composition is water based and can be formulated free of any component that might cause the composition to cause stinging when applied to a wound, free of any volatile organic compound, and free of any volatile solvent for the polyester resin other than water. Therefore, if the composition does enter the wound area, or if the composition is applied to raw or irritated skin, it will not cause stinging, and application of the composition does not result in the evaporation of volatile organic compounds such as isopropyl alcohol or dimethyl siloxane. In general, the composition will be applied to the skin in such a manner that it will be interposed between the pressure-sensitive adhesive of the dressing and the area of skin outside the wound that would otherwise be directly contacted by the adhesive when the dressing is applied to the wound. Thus, the composition is normally applied to cover an area which surrounds the wound and which is at least as large as the area which surrounds the wound that would have been contacted by the adhesive of the dressing had the dressing been properly applied to the wound without prior application of the film.

After the composition has dried, a pressure-sensitive adhesive dressing is applied thereover. The dressing may be any type of dressing which bears a layer of pressure-sensitive adhesive for adhesion to human skin. Such dressings are in the form of a web and include film dressings, foam dressings, and fabric dressings, and the adhesive layer may be continuous or discontinuous and may extend over an area substantially coextensive with the web or over one or more portions of a major surface of the web. Such dressings are well known and are in widespread use.

As noted above, the composition is very liquid and freely pourable, preferably having a viscosity of not more than 1000 cps at room temperature (72° F.). The composition includes as essential ingredients a water-dispersible film-forming polyester resin, at least one polyol plasticizer, and water. The dried film adheres well to the skin. However, bond strength between the dried film and the skin is preferably such that the bond strength between the dried film and the adhesive of the dressing which is subsequently applied is greater than the bond strength between the dried film and the skin but less than the bond strength between the adhesive of the dressing and the skin. In that event, when the dressing is removed, the film will remain adhered to the dressing and the film will separate from the skin as the dressing is removed. The force required to remove the dressing can thus be greatly reduced, for example by an amount of up to 80 or 90%, thereby reducing trauma to the skin that would result by removing a dressing that had been adhered directly to the skin. The peel strength of conventional dressings when applied directly to the skin is often more than 0.1 pounds per inch. Accordingly, it is preferred that the bond strength between the dried film and the skin is such that the force required to remove a dressing which is tenaciously bonded to the dried film, is not more than 0.1 pounds per inch, and preferably not more than 0.06 pounds per inch, and still more preferably not more than 0.05 pounds per inch. The term "bond strength" as used herein means peel strength and is determined by dividing the force (in pounds) required to peel the dressing, in a peeling direction of 180°, by the width (in inches in a direction transverse to the peeling direction) of the adhesively bonded area of the dressing. Bond strength values reported in the examples which follow are determined six hours after application of the dressing to the volar region of a person's forearm. The volar forearm region is cleaned and dried prior to application of the skin treatment composition or, in the control examples, prior to direct application of the dressing to the skin. Measurements are made using an INSTRON 4800 machine when peeling the dressing at a rate of 5 mm per second in a 180° peeling direction.

The dried film is easily removed from the skin by washing with water and a soft cloth.

The composition includes, as essential components, a water dispersible film-forming polyester resin, a polyol plasticizer, and water. Optional components include preservatives, non-ionic surfactants, friction reducing agents, detackifiers, fragrances, coloring agents and medicaments.

Preferred water-dispersible polyesters are linear polyesters having recurring sodiosulfo units having the general formula:

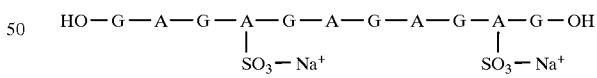

wherein A is an aromatic dicarboxylic acid moiety and G is an aliphatic or cycloaliphatic glycol moiety. Preferred polyesters and diglycol-cyclohexanedimethanol-isophthalates-sulfoisophthalates described in U.S. Pat. Nos. 3,734,874 and 3,779,993, the disclosures of which are herein incorporated by reference. Particularly preferred polyester resins of this type are available commercially from Eastern Chemical Company under the product designations such as AQ38S, AQ48S and AQ55S. The polyesters preferably have a glass transition temperature of from 30 to 60° C., and more preferably from 40 to 60° C.

The water is purified, preferably to USP grade. Suitable purification may be effected by conventional techniques such as a series of steps including carbon filtration, ion exchange, exposure to ultra violet radiation, and heating to 80° C. for 2–3 hours.

The composition also includes a plasticizer component for the polyester comprising at least one organic polyol plasticizer, preferably an aliphatic polyol plasticizer and more preferably having from 3 to 8 carbon atoms. Preferred plasticizers include glycerine, sorbitol, and propylene glycol. The amount of polyol plasticizer is suitably from 0.5 to 20% by weight, preferably 1 to 15% by weight, and more preferably 6 to 12% by weight, based on the weight of the polyester component. Most preferably, the polyol plasticizer component includes from 25–75% of glycerine and 75–25% of sorbitol. Additional plasticizers, such as triethyl citrate and triacetin may be employed, preferably in an amount of not more than 100% by weight based on the weight of the polyol plasticizer component.

The polyester is present in the composition in an amount of 20 to 35% by weight and preferably 22 to 28% by weight, based on the total weight of the polyester, the plasticizer, and water present in the composition.

The composition preferably has a microbial shelf-life of at least one year, and preferably at least two years. One or more preservatives are normally employed to ensure such shelf life. Suitable preservatives include methylparaben, imizadolidinyl urea, diazolidinyl urea, ethylparaben, propylparaben, butylparaben, sorbic acid, and sodium benzoate. The total amount of preservative effective to achieve a shelf life of at least one year and preferably at least two years will generally be in the range of about 0.5 to 2% by weight based on the weight of the composition.

The composition preferably includes one or more non-ionic surfactants, such as octoxynol-9, to enhance application of the composition to the skin. Other suitable non-ionic surfactants include polysorbate 20 and the non-ionic surfactants described in U.S. Pat. No. 5,534,247, the disclosure of which is incorporated herein by reference. Generally, an amount of 0.1 to 6% by weight of surfactant is sufficient to facilitate application of the composition to the skin.

The composition also preferably include a friction reducing agent, such as a polysiloxane which reduces the coefficient of friction of the dried film. Silicones such as Dow 193 and Dow 3225C are suitable. These particular silicones also act as a detackifier, and as a surfactant.

As mentioned above, it is an important feature of the present invention that the skin treatment composition does not require any volatile organic compound or solvent other than water. However, certain of the components of the composition, such as the surfactant, may be available commercially in a form which includes such a solvent. However, the presence of a small amount of such a solvent in the present composition, such as would result from the use of such surfactant, would not alter the essential characteristics of the composition. In its preferred form, therefore, the composition consists essentially of water, the polyester, and the plasticizer and may include minor amounts of conventional optional ingredients for skin treatment compositions such as those mentioned above as well as fragrances, coloring agents, medicaments and the like. Generally, the total amount of optional ingredients will not exceed 2–5% by weight based on the weight of the composition.

The skin treatment composition has particular use in preparing the skin for subsequent application of a pressure-sensitive adhesive dressing as described above. However, the composition may be used for other skin treatment purposes, such as to provide a protective coating on skin, as a delivery system for a topical medicament, and the like. Accordingly, the composition may include optional ingredients known to be useful in such skin treatment compositions such as medicants, preservatives, surfactants, and the other optional ingredients of the type mentioned above.

The compositions are conveniently prepared by thorough mixing of the ingredients according to procedures standard in the preparation of medicated skin treatment on skin preparation compositions. Tanks, mixers and other manufacturing equipment coming into contact with the ingredients of the skin treatment composition are generally washed with hot detergent solution, rinsed, sanitized with an antiseptic such as a chlorine solution, and again rinsed before use.

In a preferred method of preparing the composition, the purified water component and film-forming polyester resin are mixed with vigorous agitation and held at a temperature of 80° C. for about two hours. Polyol plasticizer is then added with agitation. A surfactant, a preservative, and other optional ingredients can be added at any time, provided that the temperature of the composition is sufficiently cool that efficacy of the additive will not be impaired. Agitation is preferably maintained throughout the mixing process. After cooling to about 25° C., the liquid product is packaged as such or impregnated into an appropriate applicator, such as a wipe, swab or sponge, and then packaged. A suitable wipe is provided by impregnating a rayon-polyester web (NOVONETTE) two inches long and one inch wide which is then folded in half to provide a one inch by one inch wipe which is then packaged in an air-tight foil wrap such as the type of foil packaging material described above. The amount of the liquid composition which is impregnated into the applicator is preferably such that, on application to the skin, a thin coating of the solution is applied without excess dripping. In general, an amount of about 15 to 80% by weight, based on the weight of the impregnated applicator, is suitable. Typically, an individual applicator will contain from ¼ to 2 grams of the composition.

EXAMPLES 1–12

In each of these examples, skin treatment compositions and wipes are prepared by the technique described above. The wipes contain about 0.45±0.1 grams of the composition. The wipes are then used to apply the composition to the clean, dry volar region of the forearm. Ten person panels are employed for testing each of the compositions. Drying time and characteristics of the dried film are noted and an adhesive dressing is placed over the dried film and pressed onto the dried film. Three dressings are tested: two film dressings ("OPSITE" and "IV3000") and a hydrocolloid dressing. Each dressing is three inches long and ½ inch wide and bears on one side a layer of a pressure-sensitive adhesive which covers the dressing except for a small tab area at one end of the dressing which facilitates its removal by peeling. Bond strength (i.e., peel strength) is measured as described above. The peel strength of each of the dressings when applied directly to the skin is nearly the same, and averages about 0.13 lbs/inch. The area covered by the film is larger than the adhesive area of the dressing and the dressing is positioned on the dried film such that the adhesive contacts the film only and does not directly contact the skin. After six hours, the dressing is removed by peeling from the skin and the peeling force is determined as described above.

The composition of Examples 1 to 12 is given in Table I and results are reported in Table II.

TABLE I

| Component | Ex. 1 | Ex. 2 | Ex. 3 | Ex. 4 | Ex. 5 | Ex. 6 | Ex. 7 | Ex. 8 | Ex. 9 | Ex. 10 | Ex. 11 | Ex. 12 |
|---|---|---|---|---|---|---|---|---|---|---|---|---|
| Polyester | | | | | | | | | | | | |
| AQ55S | 30 | 25 | 30 | 30 | 25 | 25 | 25 | | | | 25 | 35 |
| AQ38S | | | | | | | | 30 | 30 | | | |
| AQ48S | | | | | | | | | | 30 | | |
| Plasticizer | | | | | | | | | | | | |
| Glycerol | 2.5 | 4 | 5 | 6 | 4 | 6 | 6 | 0.5 | | 0.5 | 6 | 5 |
| Sorbitol | | 4 | 5 | 6 | 4 | 6 | | | 2 | | 6 | 5 |
| Propylene Glycol | | | | | | | 6 | | | | | |
| Water | 6S.5 | 65 | 66 | 56 | 63.5 | 58.5 | 60.55 | 67.5 | 66 | 67.5 | 61 | 53 |
| Surfactant | | | | | | | | | | | | |
| Octoxynol-9 | 2 | 2 | 2 | 2 | 2 | 2 | | 2 | 2 | 2 | | 2 |
| Polysorbate-20 | | | | | | | | | | | 2 | |
| Detackifier | | | | | | | | | | | | |
| DOW 193 | | | | | | | 2 | | | | | |
| DOW 3225C | | | | | | 2 | | | | | | |
| DOW 929 | | | | | 1.5 | | | | | | | |
| Preservative | | | | | | | | | | | | |
| Methylparaben | | | | | | | .15 | .15 | | | | |
| Germall II | | | | | | | .35 | .3 | | | | |

TABLE II

| Example | Viscosity (cps) | Drying Time (sec.) | Clarity | pH | Peel Strength lbs/in | Shelf Life yrs.[2] |
|---|---|---|---|---|---|---|
| 1 | 92 | 35 | good | 5.90 | .042 | >2 |
| 2 | 73 | 25 | good | 5.88 | .058 | >2 |
| 3 | 230 | 38 | good | 5.85 | [3] | >2 |
| 4 | 540 | 26 | good | 5.89 | [3] | >2 |
| 5 | 36 | 25 | good | 5.99 | .023 | >2 |
| 6 | 43 | 24 | good | 5.92 | .019 | >2 |
| 7 | 31 | 37 | good | 5.96 | [3] | >2 |
| 8 | 56 | 37 | poor | 6.24 | .098 | >2 |
| 9 | 55 | 35 | poor | 6.21 | [3] | >2 |
| 10 | 33 | 35 | good | 6.13 | [3] | >2 |
| 11 | 42 | 36 | good | 5.93 | [3] | >2 |
| 12 | 3500 | [1] | good | [1] | [1] | [1] |

[1]The formula is too thick and cannot be tested.
[2]Physical, chemical and microbial stability.
[3]Load cell failure, results not reliable.

In each of examples 1–12, when the dressing is removed, the underlying dried film remains adhered to the dressing and separates from the skin.

What is claimed is:

1. A method of applying a pressure-sensitive adhesive dressing to a wound which comprises:

a) applying to skin adjacent to a wound a liquid, non-stinging, water-based skin treatment composition comprising a water-dispersible film forming polyester resin, at least one polyol plasticizer, and water, said composition being freely pourable at room temperature, to form a coating of said aqueous liquid composition on said skin;

b) allowing the aqueous liquid composition to dry to form a dried adherent polymeric film on said skin, said film comprising said polyester resin and said plasticizer; and c) applying a pressure-sensitive adhesive dressing to the wound by pressing the dressing against the dried film to cause the dressing to adhere to the film.

2. A method according to claim 1 wherein the composition has a viscosity of not greater than 1000 cps at 72° F.

3. A method according to claim 1 wherein said applying of the skin treatment composition is effected by contacting the skin with an applicator impregnated with the skin treatment composition.

4. A method according to claim 3 wherein the applicator is selected from the group consisting of a wipe, a swab and a sponge.

5. A method according to claim 1 wherein said skin treatment composition has a drying time of not more than 90 seconds.

6. A method according to claim 1 wherein said polyester resin comprises a water-dispersible linear polyester having recurring sodiosulfo units of the general formula:

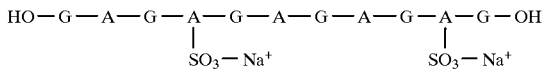

wherein A is an aromatic dicarboxylic acid moiety and G is an aliphatic or cycloaliphatic glycol residue, said polyester resin having a glass transition temperature of from 30 to 60° C.

7. A method according to claim 6 wherein said polyester resin has a glass transition temperature of from 40 to 60° C.

8. A method according to claim 7 wherein said polyol plasticizer comprises an aliphatic polyol having from 3 to 8 carbon atoms.

9. A method according to claim 8 wherein said aliphatic polyol plasticizer is selected from the group consisting of glycerine, sorbitol and propylene glycol.

10. A method according to claim 1 wherein said skin treatment composition further comprises at least one further component selected from the group consisting of a surfactant, a preservative, and a friction-reducing agent.

11. A method according to claim 1 wherein the skin treatment composition is essentially free of any volatile solvent for said polyester resin other than water.

12. A method according to claim 1 wherein said composition consists essentially of water, said polyester resin, and said plasticizer.

13. In an applicator for applying a liquid skin treatment composition to human skin, said applicator comprising a member impregnated with the composition, the improvement wherein the liquid skin treatment composition consists essentially of a freely pourable liquid, non-stinging water-based skin treatment composition consisting essentially of:

a) water;

b) a water-dispersible linear polyester having recurring sodiosulfo units of the general formula:

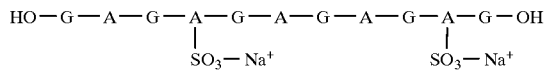

wherein A is an aromatic dicarboxylic acid moiety and G is an aliphatic or cycloaliphatic glycol residue, said polyester having a glass transition temperature of from 30 to 60° C.; and c) at least one polyol plasticizer in an amount of from 0.5 to 20% by weight based on the weight of the polyester, said polyester being present in said composition in an amount of from 20 to 35% by weight based on the weight of the polyester, the plasticizer, and water.

14. An applicator according to claim 13 wherein said member comprises a wipe, a swab, or a sponge.

15. An applicator according to claim 14 wherein said member is impregnated with from ½ to 2 grams of said composition.

16. An applicator according to claim 14 wherein said member is impregnated with from 15 to 80% by weight of said composition based on the weight of the impregnated member.

* * * * *